(12) United States Patent
Yanagita et al.

(10) Patent No.: US 7,541,593 B2
(45) Date of Patent: Jun. 2, 2009

(54) RADIATION DETECTION MODULE, PRINTED CIRCUIT BOARD, AND RADIOLOGICAL IMAGING APPARATUS

(75) Inventors: Norihito Yanagita, Hitachi (JP); Katsutoshi Tsuchiya, Hitachi (JP); Hiroshi Kitaguchi, Naka (JP); Kensuke Amemiya, Hitachinaka (JP); Yuichiro Ueno, Hitachi (JP); Kazuma Yokoi, Hitachi (JP); Ryuji Jinnai, Okinawa (JP)

(73) Assignees: Hitachi, Ltd., Tokyo (JP); Acrorad Co., Ltd., Uruma-shi (JP)

( * ) Notice: Subject to any disclaimer, the term of this patent is extended or adjusted under 35 U.S.C. 154(b) by 149 days.

(21) Appl. No.: 11/517,437

(22) Filed: Sep. 8, 2006

(65) Prior Publication Data
US 2009/0108208 A1 Apr. 30, 2009

(30) Foreign Application Priority Data
Sep. 9, 2005 (JP) ............................. 2005-263027

(51) Int. Cl.
*H01L 27/14* (2006.01)
(52) U.S. Cl. ................................. 250/370.08
(58) Field of Classification Search ............. 250/370.08
See application file for complete search history.

(56) References Cited

U.S. PATENT DOCUMENTS 6,236,051 B1    5/2001  Yamakawa et al.
7,247,860 B2 *  7/2007  Yanagita et al. ........ 250/370.09
2003/0108147 A1  6/2003  Kojima et al.
2005/0067572 A1  3/2005  Amemiya et al.
2005/0067577 A1  3/2005  Yanagita et al.

FOREIGN PATENT DOCUMENTS

| EP | 1413898 A1 * | 4/2004 |
|---|---|---|
| JP | 11-281747 | 10/1999 |
| JP | 11-304930 | 11/1999 |
| JP | 2003-084068 | 3/2003 |
| JP | 2003-167058 | 6/2003 |
| JP | 2005-106644 | 4/2005 |
| JP | 2005-106692 | 4/2005 |

* cited by examiner

*Primary Examiner*—David P Porta
*Assistant Examiner*—Shun Lee
(74) *Attorney, Agent, or Firm*—Brundidge & Stanger, P.C.

(57) ABSTRACT

There are provided a radiation detection module, a printed circuit board, and a radiological imaging apparatus which make it possible to enhance spatial resolution without increasing channel number, and thereby to perform high-accuracy diagnosis. The radiation detection module includes a plurality of radiation detectors, and a wiring board on which the plurality of radiation detectors are mounted in a manner of being arranged in at least a radiation traveling direction. Here, on the wiring board, a pair of the radiation detectors which are adjacent to each other in the radiation traveling direction are electrically connected to each other, thereby configuring one detector structure (i.e., detection channel). Moreover, the radiation detectors are mounted onto the wiring board such that respective connection parts of electrodes, which are to be electrically connected to each other, are in a mutually-facing state.

9 Claims, 7 Drawing Sheets

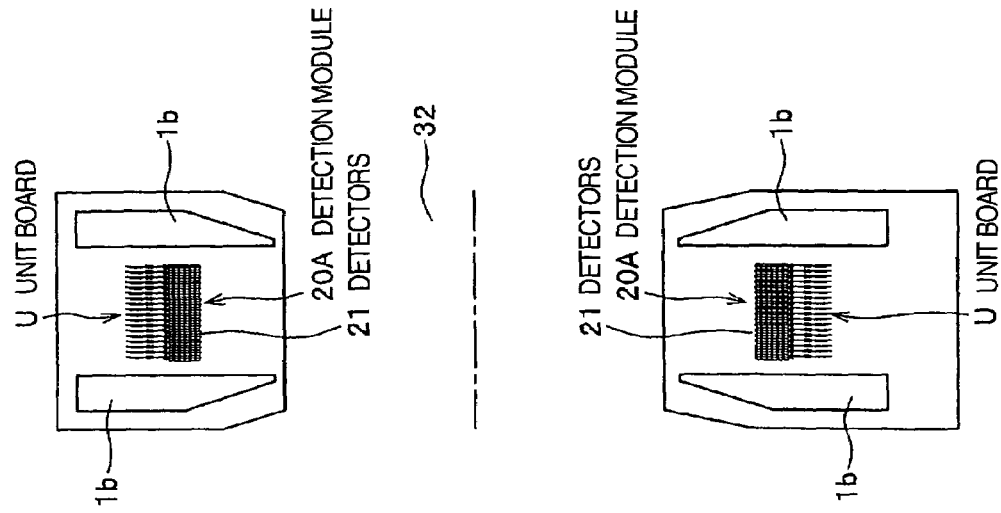
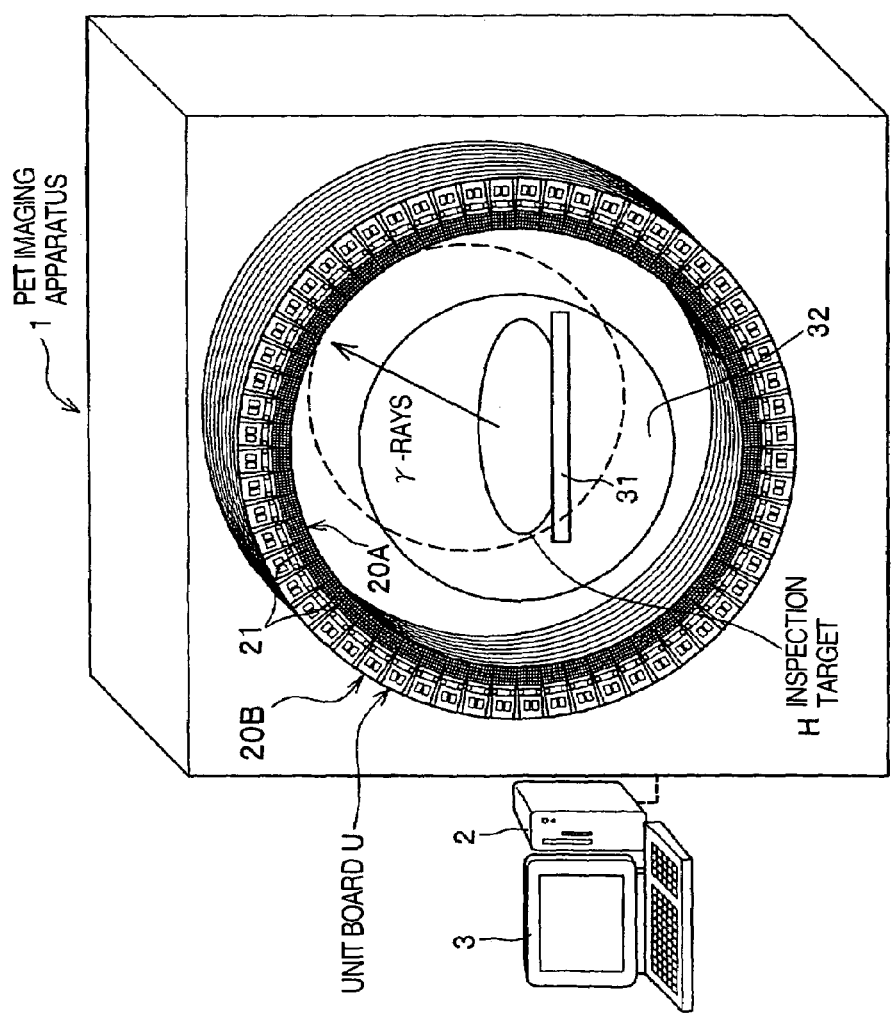

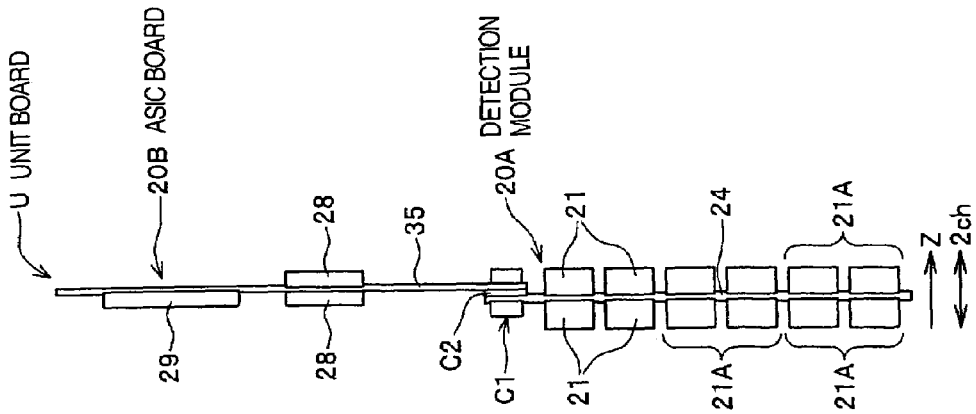
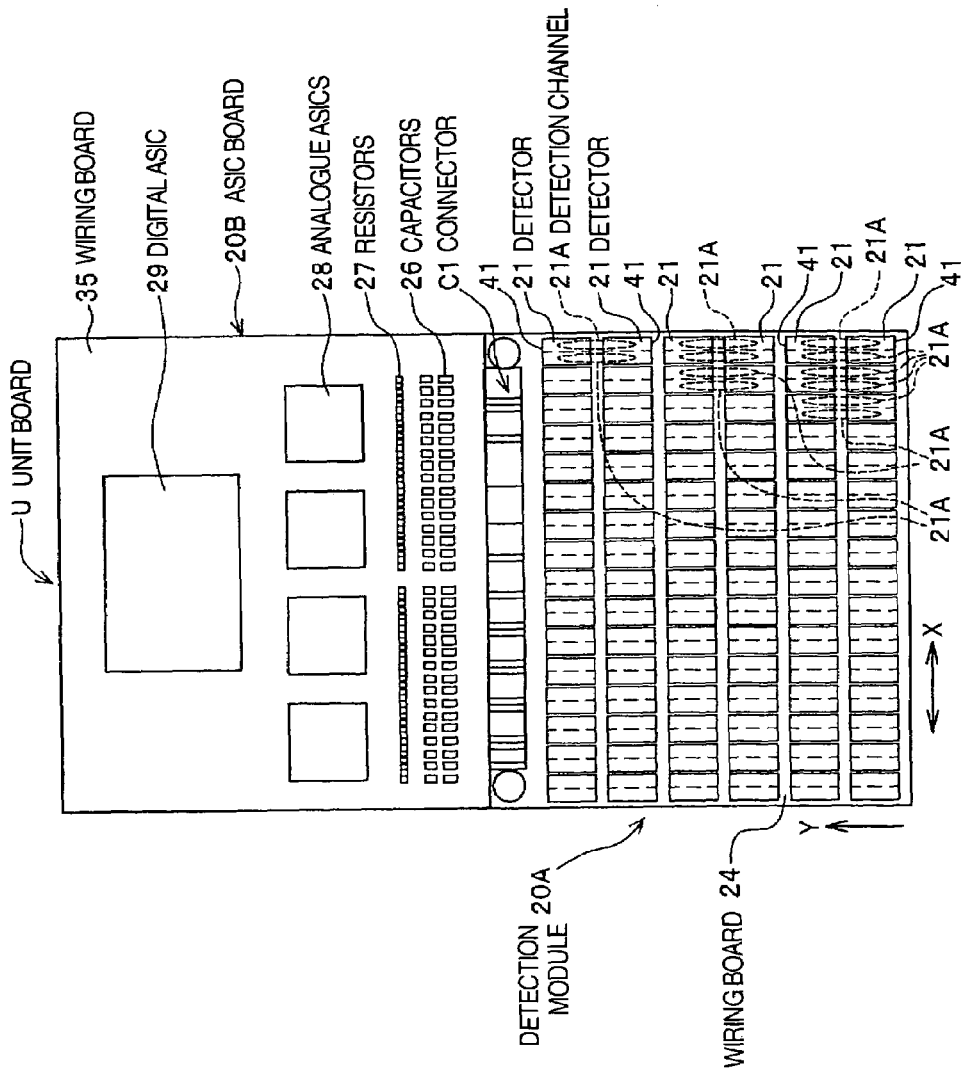

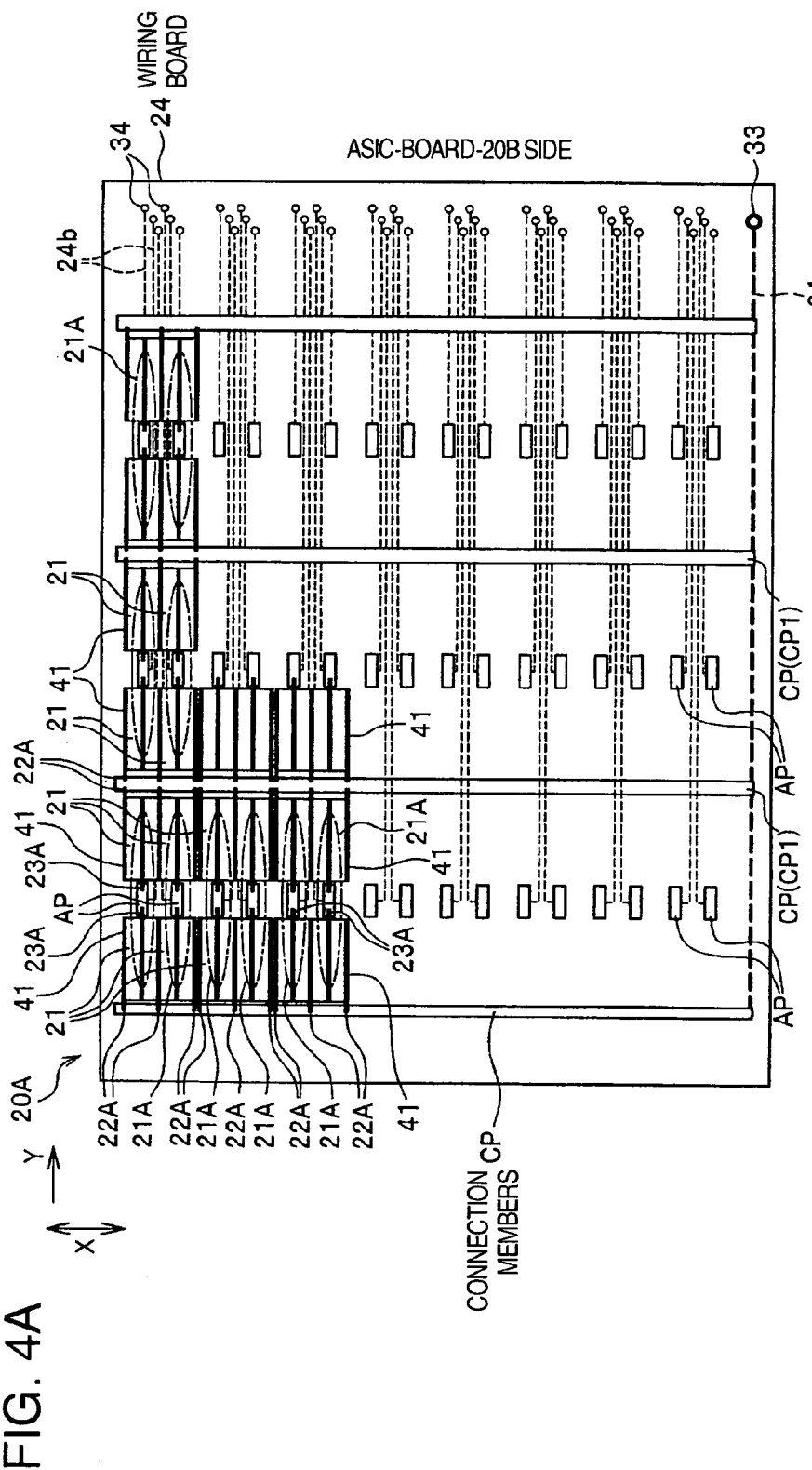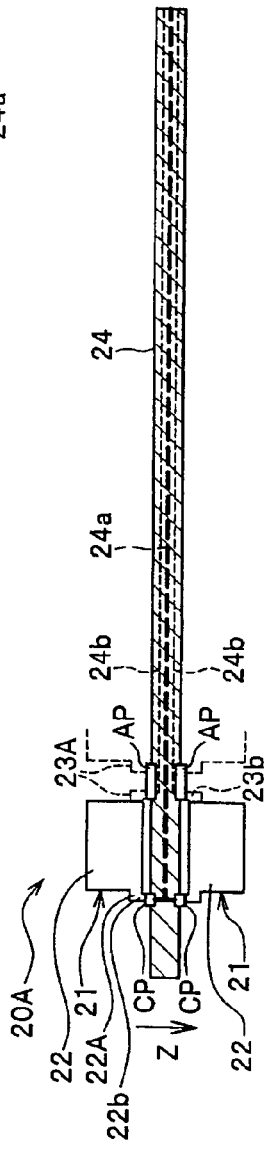
FIG. 4A
FIG. 4B

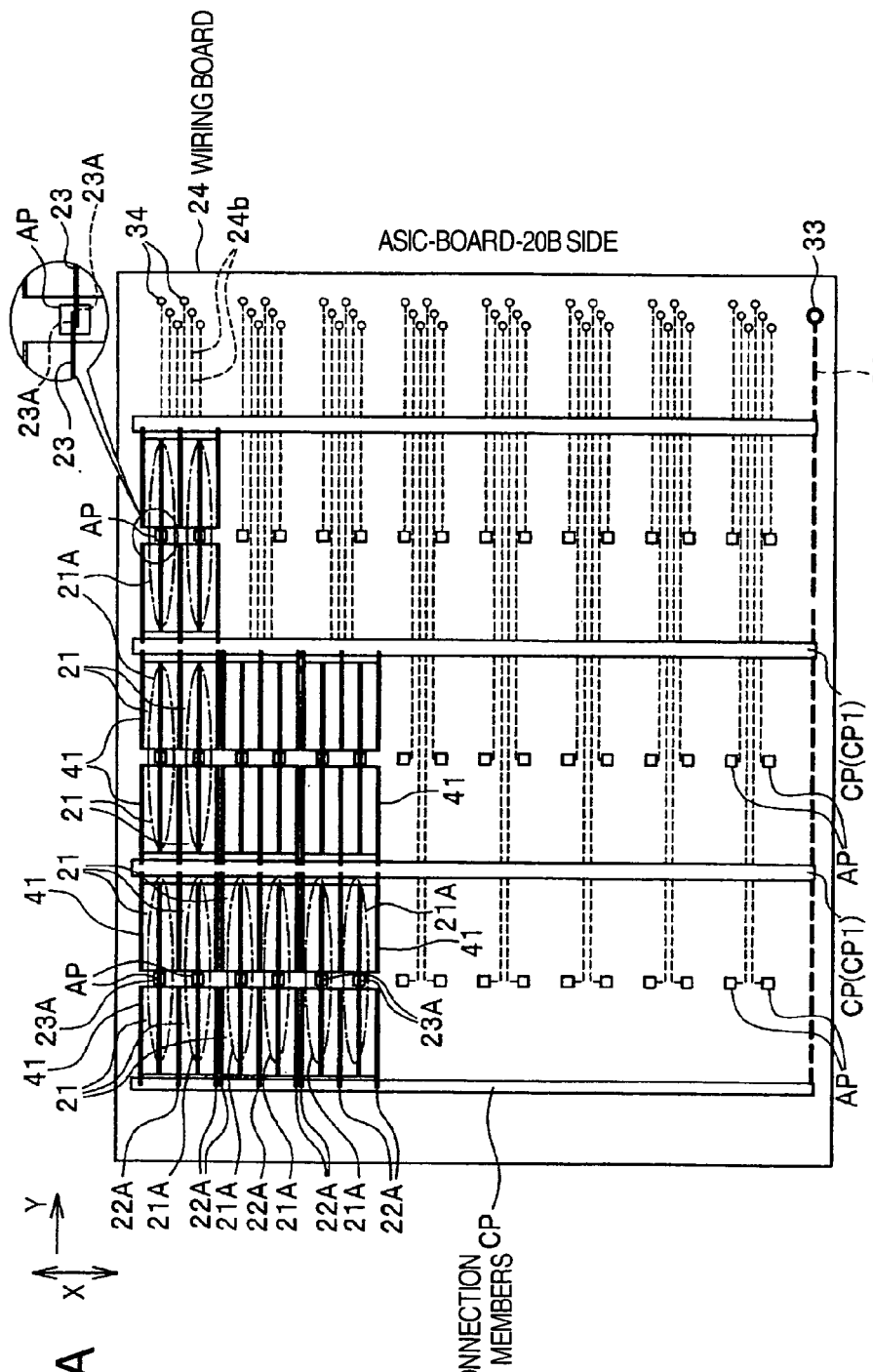
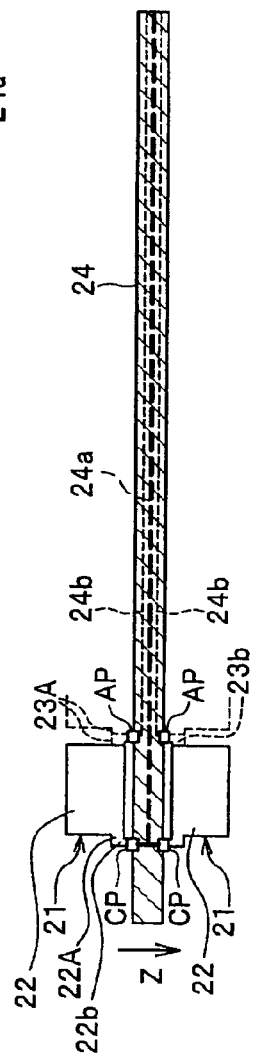
FIG. 6A
FIG. 6B

RADIATION DETECTION MODULE, PRINTED CIRCUIT BOARD, AND RADIOLOGICAL IMAGING APPARATUS

BACKGROUND OF THE INVENTION

1. Field of the Invention

The present invention relates to a radiation detection module, a printed circuit board, and a radiological imaging apparatus. More particularly, it relates to a radiation detection module, a printed circuit board, and a radiological imaging apparatus using semiconductor detection elements.

2. Description of the Related Art

Conventionally, as a radiation detector for detecting radiation such as γ-rays, there has been the semiconductor radiation detector including semiconductor detection elements. Here, the semiconductor detection elements are composed of a semiconductor material such as CdTe (cadmium telluride), CdZnTe (cadmium zinc tellurium), TlBr (thallium bromide), or GaAs (gallium arsenide). In each semiconductor detection element, electric charges, which are generated by the interaction between the radiation and the semiconductor material, are converted into electrical signals. As a result of this, the semiconductor radiation detector using the semiconductor detection elements has the following feature: Namely, as compared with the radiation detector using a scintillator, the semiconductor radiation detector exhibits a higher conversion efficiency into the electrical signals, and allows implementation of the further downsizing.

The semiconductor radiation detector includes the above-described semiconductor detection elements and electrodes formed on both sides of each semiconductor detection element. Applying a direct-current high voltage between these respective electrodes allows the electric charges to be extracted out of the electrodes as the electrical signals. Here, the electric charges are generated when the radiation such as X-rays or γ-rays has entered the inside of each semiconductor detection element.

When using the semiconductor radiation detector for a medical radiation imaging apparatus (i.e., radiological imaging apparatus), the semiconductor radiation detector is connected onto the wiring board, thereby forming a radiation detection unit (refer to, e.g., JP-A-2003-84068 (Paragraph 0024, FIG. 3)). Also, a proposal has been made concerning a technology where a plurality of semiconductor radiation detectors are arranged on a radiation-detector support plate (refer to, e.g., JP-A-2003-167058 (Paragraphs 0020 to 0021, FIG. 3)).

SUMMARY OF THE INVENTION

By the way, in order to acquire a high-accuracy image in the PET (: Positron Emission Tomography) apparatus, i.e., one type of the radiological imaging apparatuses, there exists a request for an enhancement in the spatial resolution. Also, in order to shorten the inspection time in the PET apparatus, there exists a request for an enhancement in the γ-ray detection sensitivity, e.g., an enhancement in the arrangement density of the semiconductor radiation detectors. These requests exist in the other radiological imaging apparatuses as well, such as the SPECT (: Single Photon Emission Computer Tomography) apparatus and the γ camera.

In order to implement the enhancement in the spatial resolution, it is conceivable that increasing the number of the electrical signals outputted from the semiconductor radiation detector (i.e., increasing the channel number) is preferable. Increasing the channel number as such, however, will increase the number of the processing circuits. This leads to an upsizing in the wiring board on which the processing circuits are to be mounted, as well as an increase in the power consumption. Moreover, this results in an increase in the heat-liberation amount of the wiring board as a whole. Accordingly, there has existed a danger that the detection sensitivity of the radiation detector may be lowered.

It is an object of the present invention to provide a radiation detection module, a printed circuit board, and a radiological imaging apparatus which make it possible to enhance the spatial resolution without increasing the channel number, and thereby to enhance the diagnosis accuracy.

In order to accomplish the above-described object, in the present invention, there is provided the radiation detection module including a plurality of radiation detectors, and a wiring board on which the plurality of radiation detectors are mounted in a manner of being arranged in at least a radiation traveling direction, wherein, on the wiring board, a pair of the radiation detectors which are adjacent to each other in the radiation traveling direction are electrically connected to each other, thereby configuring one detector structure (i.e., detection channel). As a result, the pair of adjacent radiation detectors can be used as the one detector structure (i.e., detection channel) which is formed in a long manner in the radiation traveling direction. Accordingly, the radiation becomes easier to capture by the amount equivalent to the long-manner-formed detection channel. Also, the detection channel, which is in this way configured by electrically connecting to each other the pair of radiation detectors adjacent to each other in the radiation traveling direction, configures one detection unit (i.e., channel). Consequently, it turns out that, substantially, the channel number in the radiation traveling direction will be decreased. Meanwhile, since the number of the detection channels increases in the X direction, the channel number in the X direction can be increased. This, in the radiological imaging apparatus, makes it possible to increase the channel number in the X direction without increasing the entire channel number. This enhances the spatial resolution of an image acquired. Also, since no increase occurs in the entire channel number, the heat-liberation increase in the signal processing circuits will be suppressed.

Also, a plurality of radiation detectors are arranged on the wiring board in a radiation traveling direction. Moreover, each radiation detector is configured by arranging a plurality of semiconductor radiation detection elements in parallel in a direction perpendicular to the radiation traveling direction, each semiconductor radiation detection element having a cathode electrode on one surface thereof, and having an anode electrode on the other surface thereof. As a result, the radiation detectors can be so configured as to detect the radiation on each radiation-detector basis in the direction perpendicular to the radiation traveling direction. Accordingly, the detection area can be fragmented in the direction perpendicular to the radiation traveling direction. This makes it possible to enhance the spatial resolution. Furthermore, between a radiation detector and another radiation detector which is adjacent to the radiation detector in the radiation traveling direction on the wiring board, either the cathode electrodes or the anode electrodes are electrically connected to each other. As a result of this connection, the radiation detector becomes a pair with another radiation detector, thereby forming one detector structure (i.e., detection channel). As a result, the pair of adjacent radiation detectors can each be used as the one detector structure (i.e., detection channel) which is formed in a long manner in the radiation traveling direction. Consequently, the radiation becomes easier to capture.

Also, by using the radiation detection module where the radiation detectors like this are provided on the wiring board, it becomes possible to acquire the radiological imaging apparatus which is superior in the spatial resolution of the image acquired for an inspection target, and which is superior in the radiation capture performance.

According to the present invention, it becomes possible to acquire the radiation detection module, the printed circuit board, and the radiological imaging apparatus which make it possible to enhance the spatial resolution without increasing the channel number, and thereby to enhance the diagnosis accuracy.

Other objects, features and advantages of the invention will become apparent from the following description of the embodiments of the invention taken in conjunction with the accompanying drawings.

BRIEF DESCRIPTION OF THE DRAWINGS

FIG. 1A is a perspective view for schematically illustrating the configuration of the PET imaging apparatus which is a preferred embodiment of the present invention, and FIG. 1B is a diagram of a bed of the PET imaging apparatus in FIG. 1A in the longitudinal direction;

FIG. 2A is a front view of a unit board used in the PET imaging apparatus illustrated in FIG. 1A, and FIG. 2B is a side view of the unit board;

FIG. 4A is a diagram for schematically illustrating the arrangement state of the plurality of radiation detectors in the detection module in FIG. 2A, and FIG. 4B is a cross-sectional view of the detection module;

FIG. 6A is a diagram for schematically illustrating the arrangement state of a plurality of radiation detectors in another detection module, and FIG. 6B is a cross-sectional view of another detection module.

DESCRIPTION OF THE INVENTION

Figure 3A:
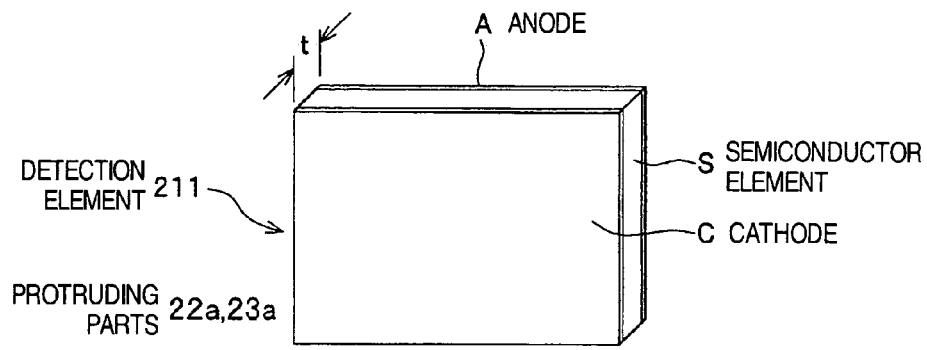
FIG. 3A is a schematically perspective view of a detection element.

Next, referring to the drawings appropriately, the detailed explanation will be given below concerning the PET apparatus, which is a preferred embodiment as a radiological imaging apparatus to which the radiation detection module including the detection channels is to be applied.

As illustrated in FIG. 1A, the PET apparatus in the present embodiment includes a PET imaging apparatus 1, a bed 31 for supporting an inspection target (i.e., inspected patient) H, a data processing apparatus (such as computer) 2, and a display apparatus 3. In the PET imaging apparatus 1, the inspection target H is mounted on the bed 31 displaceable in the longitudinal direction, then being inserted into a measurement space 32 surrounded by unit boards U.

(Pet Apparatus)

The PET imaging apparatus 1 includes the unit boards (printed circuit boards) U. The unit boards U surround the measurement space (measurement area) 32 into which the bed 31 is to be inserted, and are arranged in large number in the circumferential direction. As illustrated in FIG. 1B, the unit boards U are arranged in plural numbers in the axis direction (i.e., the longitudinal direction of the bed 31 (refer to FIG. 1A) of the measurement space 32 as well. As illustrated in FIG. 2A and FIG. 2B, each unit board U includes a radiation detection module (hereinafter, referred to as "detection module") 20A, and an integrated-circuit board (hereinafter, referred to as "ASIC board") 20B. As illustrated in FIG. 2A, the detection module 20A includes a plurality of semiconductor radiation detectors (hereinafter, referred to as just "detectors") 21 on a wiring board 24. The detectors 21 detects γ-rays emitted from inside the body of the inspection target H.

In the present embodiment, on the wiring board 24 of the detection module 20A, the plurality of detectors 21 are arranged in an orderly manner in the direction (i.e., arrow X direction in FIG. 2A; hereinafter referred to as just "X direction") which is perpendicular to the radiation traveling direction, and in the radiation traveling direction (i.e., arrow Y direction in FIG. 2A; hereinafter referred to as just "Y direction"). In the present embodiment, the spacing between the detectors 21 arranged in the X direction is made narrower than the spacing between the detectors 21 arranged in the Y direction. Namely, the detectors 21 are arranged in a densely-packed manner in the X direction. Here, the X direction corresponds to the circumferential direction in the PET imaging apparatus 1. Also, the Y direction corresponds to the radial direction (i.e., the radiation traveling direction) in the PET imaging apparatus 1 (refer to FIG. 1A). On the wiring board 24, one detection channel 21A is configured by electrically connecting to each other anode electrodes A of a pair of the detectors 21 which are adjacent to each other in the Y direction. This detection channel 21A extends in a long manner in the radiation traveling direction. The Y direction can also be said to be the direction heading from the arrangement area of the detectors 21 to that of a signal processing circuit (analogue ASIC 28). Also, the X direction can also be said to be the direction perpendicular thereto.

An ASIC board 20B includes application-specific integrated circuits (ASICs 28, 29) for measuring the peak value and detection time of γ-rays detected. Namely, the ASIC board 20B is designed to measure the peak value and detection time of the detected radiation (γ-rays). Its integrated circuits include a plurality of signal processing apparatuses for processing radiation detection signals.

Next, the explanation will be given below concerning detailed configuration components of the PET imaging apparatus 1.

(Detector Assembly Structure)

First, the explanation will be given below regarding a detector assembly structure 41 to be applied to the present embodiment. The detector assembly structure 41 includes two of the detectors 21. Each detector 21 includes two pieces of semiconductor detection elements (hereinafter, referred to as "detection elements"; refer to FIG. 3A) 211, and electrically conductive members 22, 23 (refer to FIG. 3B). As illustrated in FIG. 3A, each detection element 211 includes a semiconductor element S composed of a plate-like semiconductor material, and thin-film-like electrodes formed on the entire surfaces of both sides of the semiconductor element S by an evaporation method or the like. The electrode formed on one surface of each detection element 211 is the anode electrode (hereinafter, referred to as "anode") A, and the electrode formed on the other surface thereof is a cathode electrode (hereinafter, referred to as "cathode") C. In each detector 21, the detection elements 211 are arranged in parallel to the X direction such that the anodes A will be in a mutually-facing state. Moreover, the electrically conductive member 23 is located between these anodes A, then being fixed on these anodes A by an electrically conductive adhesive agent. These anodes A are electrically connected to each other by the electrically conductive member 23. Also, the electrically conductive member 22 is fixed on each cathode C of each detection element 211 of each detector 21 by the electrically conductive adhesive agent. In the detector assembly structure 41, the electrically conductive member 22 positioned between the adjacent cathodes C of the two detectors 21 is co-used between these two detectors 21, and is connected to these cathodes C. In the detector assembly structure 41, the anodes A and the cathodes C provided in the four pieces of detection elements 211 are alternately arranged. The electrically conductive members 22 and the electrically conductive members 23 are also alternately arranged.

The semiconductor element S is an area where electric charges are generated by the interaction between the radiation and the semiconductor material of the semiconductor element S. The semiconductor element S is composed of any one of the single crystals such as CdTe, CdZnTe, and GaAs. Also, the cathodes C and the anodes A are composed of any one of materials such as Pt, Au, and In. In the present embodiment, each detection element 211 configures a p-n junction diode, where, e.g., CdTe is used as the semiconductor element S, Pt is mainly used as the cathode C, and In is mainly used as the anode A.

Here, the explanation will be given below regarding the relationship between the time and the peak value in the thickness t of the semiconductor element S (refer to FIG. 3A). When the p-n junction reverse-direction bias voltage (hereinafter, referred to as "bias voltage") applied between the cathode C and the anode A remains one and the same value, the semiconductor element S whose thickness t is thin is quicker in the ascent (i.e., rise) of the peak value, and also accuracy of the peak value (i.e., energy resolution) becomes higher. The quicker ascent speed of the peak value enhances, e.g., accuracy of the simultaneous measurement (i.e., simultaneous count resolution) in the PET imaging apparatus 1. Namely, the semiconductor element S whose thickness t is thin becomes quicker in the ascent speed of the peak value, and also the energy resolution becomes higher (i.e., collection efficiency for electric charges becomes enhanced). This is because the time needed for the electrons to reach the anode A and the time needed for the holes to reach the cathode C are shortened each, namely, the collection time for the electric charges becomes shorter. This is also because the holes which are in danger of annihilating halfway can reach the cathode C without annihilating by the amount equivalent to the thinness of the thickness t. In this connection, the thickness t can also be expressed as the inter-electrodes distance between the cathode C and the anode A. Incidentally, the anode A is an electrode for extracting the radiation detection signals, and the cathode C is an electrode for applying the bias voltage. The thickness (the inter-electrodes distance) t of the semiconductor element S is, preferably, 0.2 mm to 2 mm.

The electrically conductive members 22, 23 are plates of, e.g., copper (or copper-mainly-constituted material such as, e.g., phosphorus bronze), and are the same as the respective electrodes of each detection element 211 in size. The electrically conductive members 22, 23 are insensitive areas which detect no radiation. Accordingly, it is desirable that the electrically conductive members 22, 23 be made thin, and be formed into a thickness which is suitable for the detection signals to be satisfactorily outputted. This thickness is equal to, e.g., about 10 μm to 100 μm, and thus basically, is equal to about 50 μm. The electrically conductive members 22, 23 include connection parts 22A, 23A for configuring one detection channel 21A (refer to FIG. 3B). In this embodiment, as will be described later, the connection parts 23A of the pair of the respective detectors 21 which are adjacent to each other in the Y direction will be electrically connected to each other. The connection parts 22A, 23A include overhanging parts 22a, 23a, which overhang onto the outer side (in the side direction, i.e., the arrow Y direction in FIG. 2A) than the semiconductor element S, and terminal parts 22b, 23b, which are perpendicularly suspended from the overhanging parts 22a, 23a. Concretely, in the detector assembly structure 41, the overhanging parts 22a of the electrically conductive members 22 connected to the cathode C are positioned on one side surface (on the left side in FIG. 3C) of each detector 21. The overhanging parts 23a of the electrically conductive members 23 connected to the anode A are positioned on the other side surface (on the right side in FIG. 3C) of each detector 21, which is the opposite side surface to the one side surface. Namely, each detector 21 has the three overhanging parts 22a (only one part is illustrated in FIG. 3C) on the one side surface, and the two overhanging parts 23a on the other side surface. The terminal parts 22b, 23b have bending parts 22c, 23c for electrically connecting the electrically conductive members 22, 23 to connection members AP or connection members CP on the wiring board 24, which will be described later.

In this way, the electrically conductive members 22, 23 also play a role as fixing members for fixing the detectors 21 onto the wiring board 24. In particular, the overhanging parts 22a, 23a become fixing parts for mounting the detectors 21 onto the wiring board 24. Incidentally, the material of the electrically conductive members 22, 23 need not be limited to copper, but may also be aluminum or aluminum alloy. Also, the configuration of the members 22, 23 need not be the plate-like configuration. Moreover, it is desirable that the electrically conductive members 22, 23 be the same as the electrodes of each detection element 211 in size, but the members 22, 23 need not be exactly the same in size.

Figure 3B:
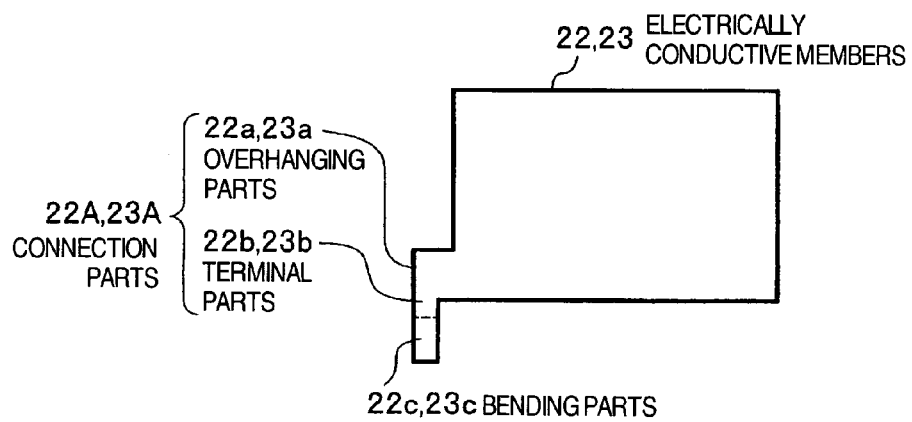
FIG. 3B is a schematic view of electrically conductive members.
Figure 3C:
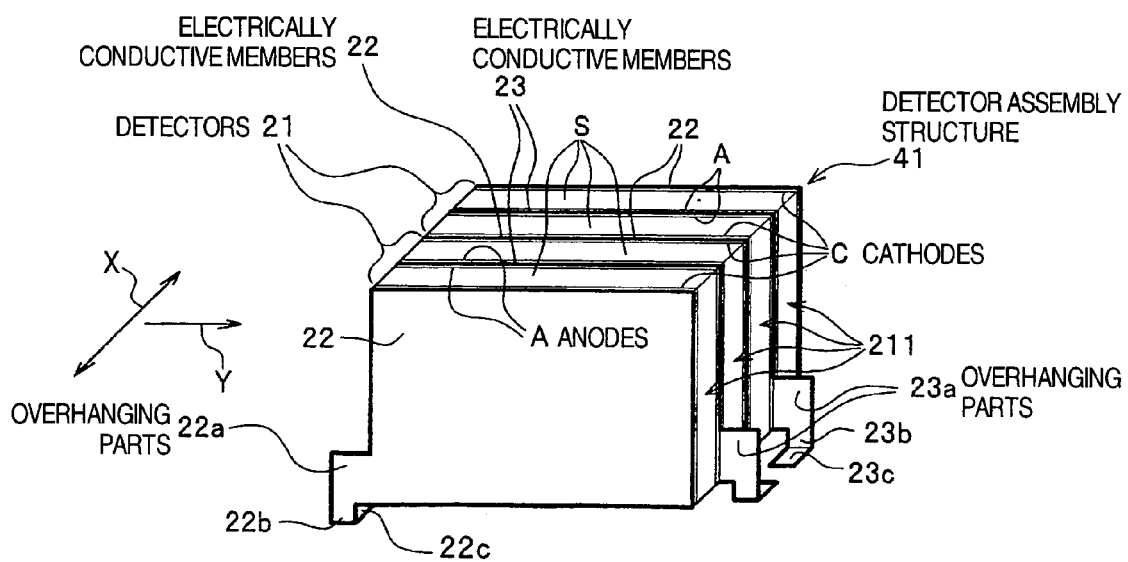
FIG. 3C is a perspective view of a semiconductor-radiation-detector assembly structure using the detection elements.

Also, as illustrated in FIG. 3B, the terminal parts 22b, 23b are formed into the narrower width so that the overhanging amounts of the terminal parts 22b, 23b become smaller than those of the overhanging parts 22a, 23a. This makes it possible to suppress the scattering of γ-rays down to the lowest possible degree in the region of the terminal parts 22b, 23b. Also, the heat conducted from the wiring board 24 to the detectors 21 decreases by the amount equivalent to the narrower-width formation of the terminal parts 22b, 23b. This enhances stability of the detectors 21.

In the present embodiment, the terminal parts 22b, 23b like this mount the detectors 21 onto the wiring board 24 in a manner of being slightly floated from the wiring board 24. Namely, the detectors 21 are mounted onto the wiring board 24 such that the bottom surface part of each detection element 211 is in a non-close-contact state with the wiring board 24. When setting up the detectors 21, this makes it possible to prevent the detectors 21 from being damaged by being rubbed on the wiring board 24. This also makes it possible to positively prevent the detectors 21 from being mounted onto the wiring board 24 in a state where the insulating property is lowered by the sandwiching of a foreign member (such as dusts) between the detectors 21 and the wiring board 24. Incidentally, a not-illustrated insulating material may be coated on bottom surface parts of the detectors 21. This, further, makes it possible to prevent an unexpected dielectric breakdown from occurring.

Figure 5:
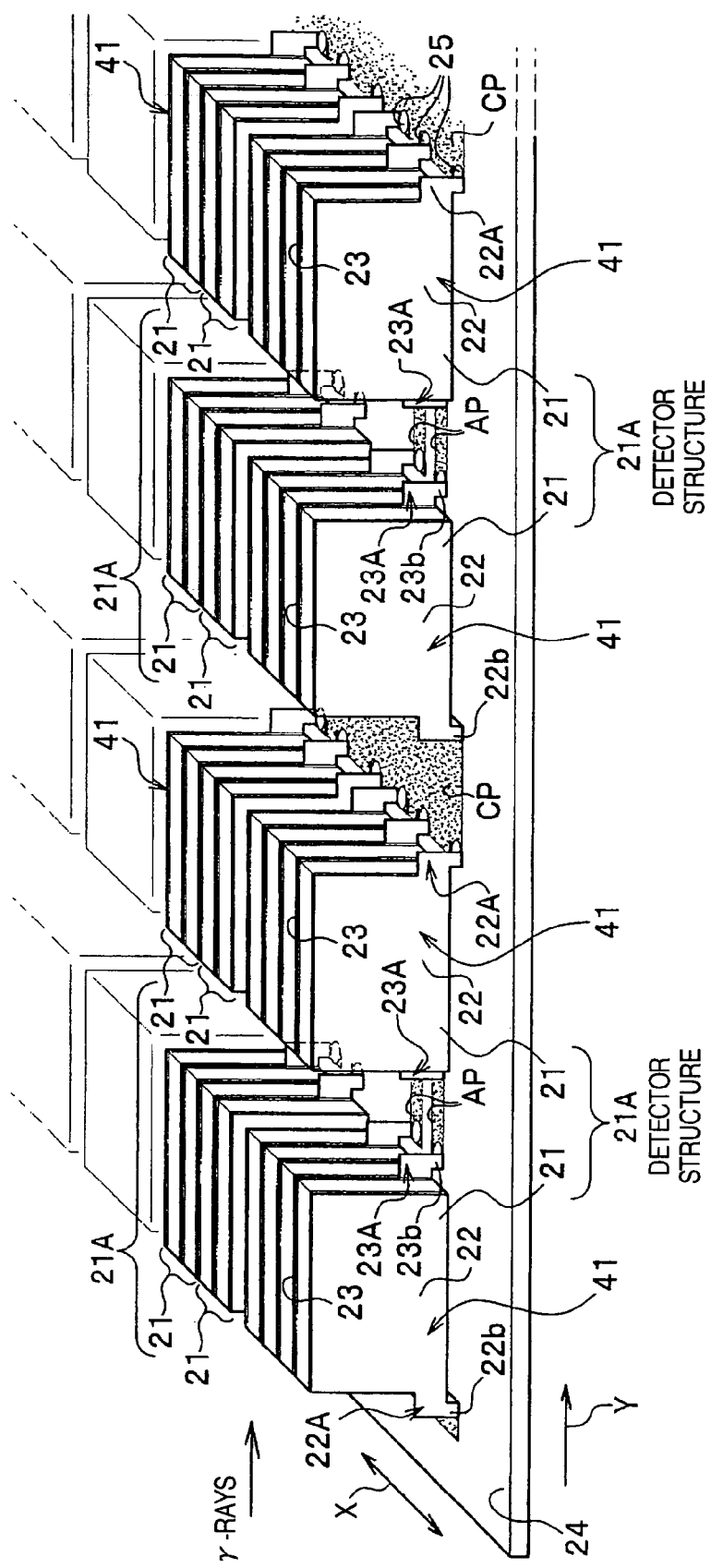
FIG. 5 is a perspective view for illustrating the arrangement state of the plurality of radiation detectors.

In the detectors 21 including the electrically conductive members 22, 23 like this, the anodes A (refer to FIG. 3C;

hereinafter, the same reference is made) of a pair of the detectors 21 which are adjacent to each other in the Y direction are electrically connected to each other via the connection parts 22A, 23A of the electrically conductive members 22, 23, thereby configuring one detection channel 21A. In such a configuration, the detectors 21 which are adjacent to each other in the Y direction are mounted onto the wiring board 24 so that the connection parts 23A of the electrically conductive members 23 connected to the anodes A will be in a mutually-facing position relationship. Concretely, as illustrated in FIG. 4A and FIG. 4B and FIG. 5, the detectors 21 are set up on the wiring board 24 in a state where, using electrically conductive adhesive agents 25, the terminal parts 23b (not illustrated in FIG. 4A, which, hereinafter, will be the same) of the connection parts 23A are electrically connected to the anode-A-used connection member (e.g., pad of the wiring board) AP provided on the wiring board 24, and where the terminal parts 22b (not illustrated in FIG. 4A, which, hereinafter, will be the same) of the connection parts 22A are electrically connected to the cathode-C-used connection member CP provided on the wiring board 24. Namely, in the pair of the detectors 21 which are adjacent to each other in the Y direction, the connection parts 23A being in the mutually-facing state are electrically connected to each other via the connection member AP on the wiring board 24.

In this way, the anodes A of the detectors 21 which are adjacent to each other in the Y direction are electrically connected to each other via the connection member AP. This connection configures the two detection channels 21A in the X direction. These detection channels 21A output the detection signals from the respective connection members AP, respectively. On the one surface of the wiring board 24, the thirty-two detection channels 21A are set up in the X direction. Here, let's make a comparison between the present embodiment and a configuration example where the detection channels 21A like this are not configured, and where the two detector assembly structures 41 are merely arranged in the Y direction. The number of the detection signals which will be outputted is two, which is common to the two cases. The present embodiment, however, outstandingly differs in a point that detecting γ-rays is made executable in the two detection channels 21A which include the two detector assembly structures 41. As a result, the channel number in the X direction becomes the double of the channel number in the X direction in the configuration example. This feature doubles the spatial resolution in the X direction. Meanwhile, as described above, the number of the detection signals which will be outputted is the same as the number of the detection signals in the case where none of the detection channels 21A is configured. Accordingly, implementing the configuration of the detection channels 21A leads to no necessity for increasing the number of the signal processing circuits. Namely, no circumstances will occur where the channel number will increase in accompaniment with the fragmentation of an area where the radiation is to be detected. This makes it possible to enhance the spatial resolution by directly using the already-existing channel number (i.e., the channel number in the case where none of the detection channels 21A is configured).

Also, in the Y direction, the detection channels 21A are formed in a long manner. This feature makes it possible to construct the detection module 20A which is superior in the radiation capture capability. Incidentally, the following configuration is not impossible: Namely, the detector assembly structure 41 is further divided in the X direction (e.g., by employing the two pieces of detection elements 211 on one piece basis), and the detectors 21 which are adjacent to each other in the Y direction are electrically connected to each other, thereby configuring the detection channels from which the detection signals are made to be outputted. Implementing such a configuration, however, gives rise to the outputting of the four detection signals in total from a pair of the detector assembly structures 41 which are adjacent to each other in the Y direction. This, eventually, results in an increase in the channel number of the detection signals, which is not preferable. In this respect, in the present embodiment, it turns out that, as described above, each detection signal is outputted from each detection channel 21A configured by the pair of the detectors 21 which are adjacent to each other in the Y direction. This feature makes it possible to implement an enhancement in the spatial resolution and an enhancement in the radiation capture capability without substantially increasing the channel number. Consequently, it becomes possible to perform the high-accuracy diagnosis which allows the finding of a small cancer. What is more, it becomes possible to avoid an upsizing in the wiring board 24 in accompaniment with an additional installment of the signal processing circuits (signal processing apparatuses). Also, there will occur no increase in the power consumption, and no high heat-liberation in the signal processing circuits.

As illustrated in FIG. 4A and FIG. 4B, the plurality of the connection members AP are set up between the pair of the detectors 21 which are adjacent to each other in the Y direction. A signal line (wiring) 24b embedded in the wiring board 24 is connected to each connection member AP. This allows each γ-ray detection signal outputted from each detection channel 21A to be outputted via each signal line 24b. The respective signal lines 24b are individually connected to a plurality of terminals 34 provided in the end part of the wiring board 24.

Also, the four connection members CP are arranged in parallel in the Y direction (i.e., the right-to-left direction in FIG. 4A) of the wiring board 24 in a state where each connection member AP is sandwiched therebetween. One and the same voltage is applied to all the connection members CP in a state where all the connection members CP are short-circuited by a wiring 24a embedded in the wiring board 24. The wiring 24a is connected to a terminal 33 provided in the end part of the wiring board 24.

In the present embodiment, as described earlier, the detectors 21 which are arranged in the Y direction such that the six detectors 21 are distributed in one column, in the two detectors 21 which are adjacent to each other in the Y direction, are arranged so that the connection parts 23A of the electrically conductive members 23 (connected to the anodes A) will be in a mutually-facing state. Then, the two detectors 21 are mounted onto the corresponding connection member AP using the electrically conductive adhesive agents 25 (refer to FIG. 5). Also, the connection parts 22A of each detector 21 are mounted onto the connection member CP using the electrically conductive adhesive agents 25. Here, in the two detectors 21 which, of the four connection members CP, are arranged on both sides of the two connection members CP1 positioned in the center and with each connection member CP1 sandwiched therebetween, the connection parts 22A of the respective electrically conductive members 22 (connected to the cathodes C) will be in a mutually-facing state. Namely, these connection members CP1 are co-used between the detectors 21 which are arranged on both sides of these connection members CP1 in the Y direction and with each connection member CP1 sandwiched therebetween.

As the adhesive agents 25, an agent such as electrically conductive paste or solder is employable. When consideration is given to the convenience for removing, from the wiring board 24, the detectors 21 which fall into an abnormal state such as malfunction, i.e., the detector assembly structure 41 in the present embodiment, it is preferable to employ a thermally plastic adhesive agent as the adhesive agents 25.

Incidentally, in each detector 21, each of the semiconductor elements S arranged in parallel has the above-described thickness t (i.e., 0.2 mm to 2 mm; refer to FIG. 3A). Also, the thickness of the cathode C and the anode A is equal to a few μm at the largest.

The above-described configuration of the detection channel 21A using the two detectors 21 is designed for accomplishing the following objects: Namely, increasing the collection efficiency for the electric charges by making the thickness t (refer to FIG. 3A) of the semiconductor element S thin, enhancing the energy resolution by increasing the ascent speed of the peak value, and also increasing the interaction between the semiconductor element S and γ-rays (i.e., increasing the count number of γ-rays) by taking advantage of the in-parallel arrangement of the semiconductor elements S thereby to reduce the quantity of the γ-rays which will merely pass through the semiconductor elements S without being captured thereby. The increase in the count number of γ-rays gives rise to an enhancement in the sensitivity of the detection channel 21A.

Here, the explanation will be given below concerning the outline of the detection principle of γ-rays using the detection channel 21A. When γ-rays enters the detection channel 21A from the Y direction, and the semiconductor element S and γ-rays exert the interaction therebetween, the holes and the electrons are generated in pairs by the quantity which is proportional to an energy that γ-rays has. By the way, the charges-collecting bias voltage (e.g., a reverse-direction applied voltage where the cathode C is at −500 V and the anode A is at an electric potential close to the ground potential, i.e., the anode A is higher than the cathode C by 500 V) from a direct-voltage high-voltage power supply (not illustrated) is applied between the electrodes of the cathode C and the anode A of each of the detection elements 211 which configure the detection channel 21A. On account of this, the holes, which are equivalent to positive charges, displace by being attracted by the cathode C, while the electrons, which are negative charges, displace by being attracted by the anode A. When making a comparison between these holes and electrons, the electrons are relatively higher than the holes in their ease of displacement (i.e., their mobility). Accordingly, it turns out that the electrons reach the anode A in a relatively shorter time. Meanwhile, the holes are relatively lower in their ease of displacement. Consequently, it turns out that the holes reach the cathode C in a relatively longer time. In this connection, there are some cases where the holes are captured (i.e., trapped) halfway before reaching the cathode C.

In the detection channel 21A, the electrically conductive members 23 arranged between the anodes A, and the electrically conductive members 22 mounted onto the cathodes C become insensitive areas which detect no γ-rays. Incidentally, the anodes A and the cathodes C themselves are also the insensitive areas.

According to the above-described arrangement of the detection channels 21A, as illustrated in FIG. 2A and FIG. 2B, the number of the channels arranged on the wiring board 24 of the detection module 20A is as follows: Namely, 3 ch in the Y direction (i.e., radial direction of the PET imaging apparatus 1) heading from the detection module 20A to the ASIC board 20B, 32 ch in the X direction (i.e., circumferential direction of the PET imaging apparatus 1) perpendicular to the Y direction, and 2 ch (on both sides of the wiring board 24) in the Z direction (i.e., deep direction of the PET imaging apparatus 1) which is the thickness direction of the wiring board 24. Accordingly, it turns out that the detection channels 21A are set up on one side of the wiring board 24 in the number of 96 in total, and are set up on both sides thereof in the number of 192 in total.

In the detection module 20A in the present embodiment, three configurations as will be explained hereinafter make it possible to enhance the arrangement density of the detectors 21. This allows accomplishment of the high-accuracy implementation of the detection channels 21A.

The first configuration is as follows: Namely, the respective detectors 21 are arranged such that the connection parts 22A, 23A will be directed into the Y direction. This prevents the connection parts 22A, 23A from being directed into the X direction, thereby making it possible to narrow the spacing between the mutual detectors 21 in the X direction. This, in accompaniment with the feature that each detection channel 21A is configured by the two detectors 21 which are adjacent to each other in the Y direction, makes it possible to enhance the resolution of an inspection target H (refer to FIG. 1A) in the body-axis-around direction (X direction).

Also, the second configuration is as follows: Namely, the respective detectors 21 are arranged such that, in the X direction, the same-polarity electrodes (e.g., the cathodes C) will be in a mutually-facing state. This arrangement makes it possible to reduce the insulation between the mutual detectors 21 in the X direction, thereby making it possible to narrow the spacing between the mutual detectors 21 in the X direction. In particular, the two detectors 21 arranged in the X direction configure the detector assembly structure 41 which co-uses one cathode C. This makes it possible to accomplish the densely-packed implementation of the detectors 21 in the X direction.

Furthermore, the third configuration is as follows: Namely, the two detectors 21 which are adjacent to each other in the Y direction are arranged such that the connection parts 22A, 23A (i.e., electrical connection parts of the detectors 21 with the outside) connected to the same-polarity electrodes (i.e., the anodes A or cathodes C) will be in a mutually-facing state. This arrangement makes it possible to reduce the insulation between the mutual detectors 21 in the Y direction, thereby making it possible to narrow the spacing between the mutual detectors 21 in the Y direction. This, further, makes it possible to accomplish the densely-packed implementation of the detectors 21 in the Y direction.

In the above-described first and second configurations each, the spacing between the mutual detectors 21 in the X direction is narrowed. As a result, when γ-rays emitted from inside the body of the inspection target H on the bed 31 travels from below to above (Y direction, i.e., radial direction of the PET imaging apparatus 1; refer to FIG. 1A and FIG. 1B) in FIG. 2A, it becomes possible to reduce the ratio of γ-rays which will merely pass through the detectors 21 without being captured and detected by the detectors 21 (i.e., the γ-rays which passes through the spacing formed between the detectors 21 adjacent to each other). Accordingly, the first and second configurations each allow an enhancement in the γ-ray detection efficiency, and allow an enhancement in the spatial resolution of an image acquired. Also, it becomes possible to acquire an advantage of being capable of shortening the inspection time.

Also, in the above-described third configuration, the spacing between the mutual detectors 21 in the Y direction is narrowed. As a result, it becomes possible to reduce the ratio at which γ-rays, which travels obliquely with respect to the wiring board 24 in the Y direction, will merely pass through the spacing between the mutual detectors 21 in the Y direction. Consequently, this third configuration, similarly to the first and second configurations, also allows an enhancement in the γ-ray detection efficiency, and allows an enhancement in the spatial resolution of an image. Also, this third configuration is capable of making a contribution to shortening the inspection time.

In this way, the detection module 20A having the first, second, and third configurations allows an enhancement in the γ-ray detection efficiency, and allows an enhancement in the spatial resolution of an image.

In the present embodiment, the detectors 21 are set up on both sides of the wiring board 24. As a result, as compared with the case where the detectors 21 are set up on only one side of the wiring board 24, it becomes possible to reduce the number of the wiring boards 24 down to the one-half. Here, the wiring boards 24 are to be arranged in the deep direction (i.e., Z direction) of the PET imaging apparatus 1. This makes it possible to arrange the detectors 21 in a more densely-packed manner in the Z direction. This case also allows an enhancement in the γ-ray detection efficiency, and allows making a contribution to an enhancement in the spatial resolution of an image. In accompaniment therewith, as described above, it becomes possible to reduce the number of the wiring boards 24 (unit boards U) down to the one-half. Accordingly, there also exists a merit of being capable of saving a time and labor for a task such as setting up the unit boards U on the PET imaging apparatus 1 (refer to FIG. 1A).

By the way, it is preferable to avoid the dielectric breakdown of the detectors 21 by coating the detectors 21 with an insulating material. The coating film of the insulating material can be formed into thickness of a few μm by soaking the detectors 21 into the insulating material such silicon rubber all along with the detection module 20A, and by drying them afterwards. In this case, the following methods are also allowable: After having coated the detectors 21 with the dielectric coating film with the exclusion of portions of the connection parts 22A, 23A, the terminal parts 22b, 23b of the connection parts 22A, 23A are mounted onto the corresponding connection members AP, CP on the wiring board 24. The electrically conductive members 22, 23 are formed into a size which is smaller than the detection elements 211, and a portion of the overhanging parts 22a, 23a is positioned between the detection elements 211. This is performed in order to reduce a danger of the dielectric breakdown of the electrically conductive members 22, 23 with the connection members AP, CP of the electrodes in a mutually-facing state therewith.

Also, as illustrated in FIG. 6A and FIG. 6B, the connection parts 22A, 23A of the detectors 21 which are adjacent to each other in the Y direction may also be connected to the connection member AP on the wiring board 24 in a state where the connection parts 22A, 23A are overlapped with each other. Implementing this configuration allows implementation of more-proximate arrangement of the detectors 21 in the Y direction, thereby making it possible to arrange the detectors 21 in an even more densely-packed manner in the Y direction. Also, it becomes possible to downsize formation area of the connection members AP on the wiring board 24, thereby allowing implementation of an enhancement in the insulating property.

Figure 7:
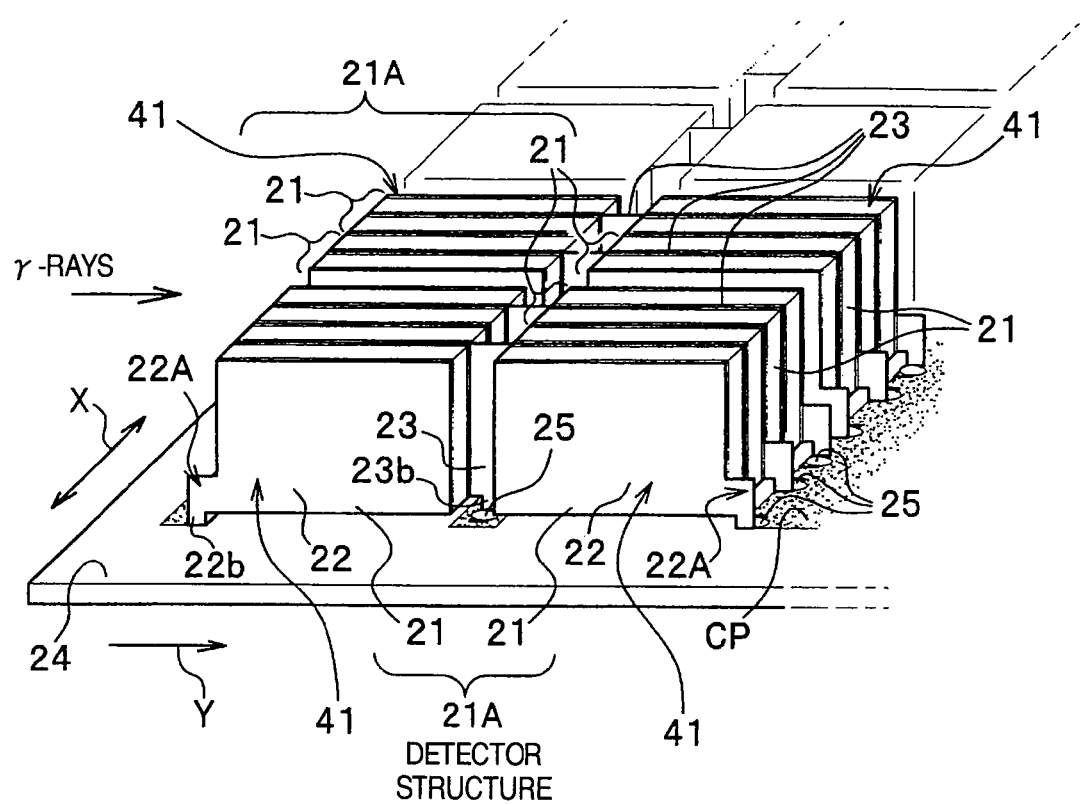
FIG. 7 is a perspective view for illustrating the arrangement state of the plurality of radiation detectors in another detection module.

Moreover, as illustrated in FIG. 7, each electrically conductive member 23 may be formed into a size which is basically equal to the adjacent detectors 21, thereby co-using each electrically conductive member 23 between the detectors 21. Implementing this configuration makes it possible to further shorten the distance between the adjacent detectors 21 in the Y direction, thereby allowing accomplishment of the densely-packed implementation of the detectors 21 on the wiring board 24. Also, the pair of the detectors 21 are connected to each other via the electrically conductive member 23, which enhances rigidity of the detection channel 21A. Also, positioning of the densely-packed implementation onto the wiring board 24 is easy to perform, which enhances the mounting accuracy.

Also, although not illustrated, the following configuration is also possible: Namely, in the detector assembly structures 41 which are adjacent to each other in the X direction, the cathodes C positioned at both ends thereof are co-used by a piece of electrically conductive member 22. In this way, a plurality of detector assembly structures 41 are integrated, thereby configuring a larger detector assembly structure 41 in the X direction. This configuration allows the adjacent electrically conductive members 22 (cathodes C) to be decreased on each piece of electrically conductive member basis in the detector assembly structures 41 which are adjacent to each other in the X direction in FIG. 2A. The space by the amount equivalent to the decreased members 22 makes it possible to increase the number of the detectors 21 in the X direction. Consequently, it becomes possible to accomplish the densely-packed implementation of the detectors 21 on the wiring board 24. This densely-packed implementation can be accomplished by employing an even number as the number of the detection elements 211 configuring the detector assembly structure 41, and by employing the cathodes C as the electrodes arranged at the mutually face-to-face ends of each detector assembly structure 41.

In the case like this as well where the larger detector assembly structure 41 is used in the X direction, the anodes A of the detectors 21 which are adjacent to each other in the Y direction are electrically connected to each other via the connection parts 22A, 23A of the electrically conductive members 22, 23. This makes it possible to configure the plurality of one large detection channel 21A. Implementing the detection channel 21A like this allows implementation of the densely-packed arrangement of the detectors 21 in the X direction and the Y direction.

(Unit Board)

Next, referring to FIG. 2A and FIG. 2B, the explanation will be given below concerning the detailed structure of the unit board U. The unit board U includes the detection module 20A on which the detection channels 21A are set up as described above, and the ASIC board 20B. The ASIC board 20B includes capacitors 26, resistors 27, analogue ASICs 28, and a digital ASIC 29.

(Detection Module)

As illustrated in FIG. 4A and FIG. 4B, the detection module 20A is configured by forming the detection channels 21A by setting up the plurality of detectors 21 on the wiring board 24. As described earlier, the bias voltage of, e.g., 500 V, is applied between the anode A and the cathode C of each detector 21 for the charge collection. This voltage is applied between the anode A and the cathode C of each detector 21 via a power-supply-used wiring (not illustrated) set up on the wiring board 24 of the detection module 20A via a connector C1 from a power-supply-used wiring (not illustrated) set up on the ASIC board 20B. The detection module 20A includes the connector C1 (refer to FIG. 2A and FIG. 2B; hereinafter, the same reference is made) at the end portion of the wiring board 24. The connector C1 includes the above-described terminal 33 and a plurality of terminals 34. Each γ-ray detection signal outputted from each detection channel 21A is supplied to the ASIC-board-20B side via the connector C1.

(ASIC Board)

On the ASIC board 20B, as illustrated in FIG. 2A and FIG. 2B, the eight analogue ASICs 28 are set up on both sides of a wiring board (support board) 35 (four on one side thereof). Also, one digital ASIC 29 is set up on one side of the wiring board 35. Also, on both sides of the wiring board 35, the capacitors 26 and the resistors 27 are set up in the number of the detection channels 21A. A plurality of connection wirings (not illustrated) for electrically connecting these capacitors 26, resistors 27, analogue ASICs 28, and digital ASIC 29 are provided in the wiring board 35. These connection wirings are formed into a multi-layered structure in the wiring board 35. The arrangement of the capacitors 26, analogue ASICs 28, and digital ASIC 29 in the wiring board 35 is so set as to correspond to the order in which the signal supplied from each detector 21 of the detection module 20A is transferred. The resistors 27 are connected to a ground wiring (not illustrated) one side of which is connected to the input side of the capacitors 26 and the other side of which is provided in the wiring board 35. The analogue ASICs 28, which are one type of LSIs, mean ASICs (: Application-Specific Integrated Circuits) for processing the analogue signal (i.e., each γ-ray detection signal) outputted from each detection channel 21A. In the analogue ASICs 28, a signal processing circuit (signal processing apparatus) is provided for each detection channel 21A. Each of these signal processing circuits inputs the γ-ray detection signal (radiation detection signal) outputted from the corresponding one detection channel 21A, then determining the peak value of γ-rays. The ASIC board 20B includes, at the end portion of the wiring board 35, a connector C2 which has a plurality of terminals connected to the respective capacitors 26.

The unit boards U are set up on a ring-shaped support member 1b (part of which is illustrated in FIG. 1B) set up on the PET imaging apparatus 1, such that the surfaces on which the detectors 21 are set up are directed into the deep direction (i.e., the longitudinal direction of the bed 31, and the Z direction in FIG. 2B) of the PET imaging apparatus 1. This ring-shaped support member 1b is provided such that the member 1b surrounds the circumference of the measurement space 32. The unit boards U set up on the ring-shaped support member 1b are arranged in the circumferential direction. This allows the unit boards U to surround the measurement space 32. Moreover, the unit boards U are arranged such that the detection module 20A is positioned on the inner side (the measurement-space-32 side), and such that the ASIC board 20B is positioned on the outer side. In the present embodiment, the unit boards U are arranged in plural numbers in the deep direction of the PET imaging apparatus 1 as well. In the unit boards U set up in this way, the X direction illustrated in FIG. 2A, FIG. 3C, and the like becomes the circumferential direction (circumferential direction of the ring-shaped support member) of the PET imaging apparatus 1. Also, the Y direction illustrated in FIG. 2A, FIG. 3C, and the like becomes the radial direction (radial direction of the ring-shaped support member) of the PET imaging apparatus 1.

(Connection Structure of Detection Module and ASIC Board)

As illustrated in FIG. 2B, the detection module 20A and the ASIC board 20B are assembled by overlapping end portions of the detection module 20A and the ASIC board 20B with each other, and connecting the connector C1 and the connector C2 to each other which exist at this overlapped portion. The end portion of the detection module 20A and that of the ASIC board 20B are connected to each other at the overlapped portion in a freely detachable/attachable (i.e., freely removable/connectable) manner by using a fastening screw or the like. The reason why the end portions need to be connected at the overlapped portion is as follows: Namely, each unit board U on which the detection module 20A and the ASIC board 20B are connected to each other is supported in a one-side-held manner. As a result, depending on the set-up position of each unit board U, a force which will warp or bend each unit board U is exerted onto the central portion (i.e., the connection portion) thereof. Here, if the connection portion is formed into a structure that the end surface of the wiring board 24 and that of the wiring board 35 are made to butt to each other, the connection portion is exceedingly likely to be warped or bent, which is not preferable.

Taking this point into consideration, in the present embodiment, the detection module 20A and the ASIC board 20B are assembled in the above-described manner of being connected to each other at the overlapped portion. On account of this feature, as compared with the structure that the end surface of the wiring board 24 and that of the wiring board 35 are connected in the manner of being made to butt to each other, each unit board U used in the present embodiment is enhanced in the robustness against the warp or bend. This enhancement in the robustness of each unit board U against the warp or bend, e.g., suppresses position shifts of the detectors 21, thereby enhancing the accuracy in identifying γ-ray generation positions. In this connection, as illustrated in FIG. 1A, in the PET imaging apparatus 1, the unit boards U are arranged in large number in the circumferential direction and in the deep direction. Accordingly, a unit board U positioned at the right-side or left-side portion (at the directly-horizontal portion in particular) in FIG. 1A becomes more likely to be warped or bent. For this reason, the robustness of the unit boards U against the warp or bend becomes important. In particular, each detection channel 21A is configured by electrically connecting to each other the two detectors 21 which are adjacent to each other in the Y direction as illustrated in FIG. 2A, FIG. 3C, and the like. Consequently, the above-described enhancement in the robustness of each unit board U against the warp or bend effectively maintains the electrical connection in each detection channel 21A, and also ensures the mount-on accuracy of the size between the detectors 21 or the like. As a consequence, each detection channel 21A becomes exceedingly unlikely to be influenced by the time-elapsed change or the like. This makes it possible to acquire high-accuracy PET images in a considerable long time.

Taking advantage of the above-described electrical connection structure of the detection module 20A and the ASIC board 20B via the connector C1 and the connector C2, it becomes possible to transfer the γ-ray detection signals from the detection module 20A to the ASIC board 20B with a low loss. In this connection, the implementation of a low loss enhances, e.g., the energy resolution in each detector 21.

The detection module 20A is mounted onto the ASIC board 20B in the freely detachable/attachable manner by using a screw or the like. Accordingly, e.g., if a malfunction such as detection failure occurs in the detectors 21 or the ASICs 28, 29, it suffices to replace only the portion where the malfunction exits (i.e., the detection module 20A or the ASIC board 20B). Incidentally, the electrical connection of the detection module 20A and the ASIC board 20B is implemented by using the connector C1 such as the spring pin connector. This feature makes it easy to establish the connection and release of the connection (i.e., the link and release of the link) between the boards, and also makes it possible to ensure the mount-on accuracy easily. Although, in the above-described configuration, the single detection module 20A is connected to the ASIC board 20B, the single detection module 20A may also be divided into a plurality of modules.

The shorter the lengths of the circuits or the lengths (distances) of the wirings for transferring the γ-ray detection signals become, the smaller the influences of noises or the attenuation of the signals halfway become, and the more preferable the lengths of the circuits or the wirings are. Also, when performing the simultaneous measurement processing in the PET imaging apparatus 1, the shorter the lengths of the circuits or the wirings become, the less the time delay becomes, and the more preferable the lengths of the circuits or the wirings are (the more preferable because accuracy of the detection time is not damaged). On account of this, in the present embodiment, the order of the arrangement of the detectors 21, capacitors 26, analogue ASICs 28, and digital ASIC 29 on the unit board U is so set as to correspond to the direction heading from the central axis to the outer side in the radial direction of the PET imaging apparatus 1. This configuration makes it possible to shorten the lengths (distances) of the wirings for transferring the extremely-weak γ-ray detection signals outputted from the detectors 21 to amplifiers of the analogue ASICs. This reduces the influences of noises on the γ-ray detection signals, and lowers the attenuation of the γ-ray detection signals.

Also, it is possible to provide the capacitors 26 and the resistors 27 inside the analogue ASICs 28. In the present embodiment, however, the capacitors 26 and the resistors 27 are located outside the analogue ASICs 28. The reason for this configuration is, e.g., acquiring proper capacity value and proper resistance value. Incidentally, the capacitors 26, the resistors 27, and the analogue ASICs 28 provided on the ASIC board 20B may also be provided not on the ASIC board 20B but on the detection module 20A. In this case, the capacitors 26, the resistors 27, and the analogue ASICs 28 are positioned more on the ASIC-board-20B side than the detector-21 side. Since the detection module 20A includes the detectors 21 and the analogue ASICs 28, it becomes possible to shorten the distances (lengths of the wirings) between the detectors 21 and the analogue ASICs 28 even further. This reduces the influences of noises even further.

(Operation of PET Imaging Apparatus)

Next, the explanation will be given below regarding the operation of the PET imaging apparatus 1 which has the configuration explained so far. Before making the radiation inspection, at first, a PET-used radioactive medication (including, e.g., $^{18}$F) is dosed in advance into the inspection target H using a method such as injection so that its in-body dosage radioactivity will become equal to, e.g., about 370 MBq. The radioactive medication is selected depending on the inspection object (such as identifying position of cancer, or inspection on aneurysm of heart). The radioactive medication dosed, eventually, will be accumulated into an affected area of the inspection target H. The inspection target H in this state is advised to lie on the bed 31.

Depending on the inspection object, the inspector (i.e., diagnostic radiation technician or medical doctor) who is going to execute the PET inspection inputs necessary information (such as area whose tomography image the inspector wishes to acquire (imaging area or concern area), slice number, slice spacing, and absorbed dosage) via the data processing apparatus 2 (refer to FIG. 1A). In this case, the inspector can employ the methodology of causing a not-illustrated information input screen to be displayed on the display apparatus 3, then inputting the necessary data by using keyboard and mouse. After that, the inspector displaces the bed 31 in the longitudinal direction, thereby inserting the inspection target H into the measurement space 32 until the inspection region (e.g., affected area of cancer) of the inspection target H has reached a predetermined position.

Based on the instruction from the data processing apparatus 2, the direct-voltage high voltage is applied between the anode A and the cathode C of each of the detectors 21 which configure the detection channel 21A. This allows the PET imaging apparatus 1 to start the PET inspection. The γ-rays emitted from inside body of the inspection target H by the radioactive medication is detected by the detection channels 21A (concretely, the detectors 21 inside each of the detection channels 21A). Namely, at the time of annihilation of one positron emitted from the PET-used radioactive medication, a pair of γ-rays are emitted in mutually opposite directions which form about 180°, then being detected by different two detection channels 21A. Each of the two detection channels 21A outputs a γ-ray detection signal. This γ-ray detection signal passes through the signal lines 24b, the connectors C1, C2, and the capacitors 26, then being inputted into the corresponding signal processing circuit (not illustrated) inside the analogue ASICs 28. This signal processing circuit amplifies the γ-ray detection signal, then determining the peak value of the γ-rays detected. This peak value is converted into digital peak-value information by a not-illustrated analogue/digital converter (ADC) on the ASIC board 20B. Furthermore, the digital ASIC 29 also outputs position information on each of the two detection channels 21A which have detected the pair of γ-rays, and information on γ-ray detection times. The digital peak-value information, the position information on each of the two detection channels 21A which have detected the pair of γ-rays, and the γ-ray detection-time information are inputted into the data processing apparatus 2. Taking advantage of the γ-ray detection-time information, the simultaneous measurement apparatus (not illustrated) of the data processing apparatus 2 counts, as one, the pair of γ-rays generated by the annihilation of the one positron. Moreover, based on the position information on each of the two detection channels 21A which have detected the pair of γ-rays, the simultaneous measurement apparatus identifies the position of each of the two detection channels 21A. Also, taking advantage of the count value and the position information on each detection channel 21A, a tomography-image information creation apparatus (not illustrated), which is the image-information creation apparatus of the data processing apparatus 2, creates the tomography-image information (i.e., image information) on the inspected patient at the accumulation position of the radioactive medication, i.e., the position of the malignant tumor. This tomography-image information will be displayed on the display apparatus 3.

Hereinafter, the explanation will be given below concerning effects which are acquirable in the present embodiment.

(1) In the present embodiment, on the wiring board 24, the pair of the radiation detectors 21 which are adjacent to each other in the Y direction are electrically connected to each other, thereby configuring the one detection channel 21A. As a result, the pair of adjacent radiation detectors 21 can be used as the one detection channel 21A which is formed in a long manner in the Y direction. Accordingly, the radiation becomes easier to capture by the amount equivalent to the long-manner-formed detection channel. In the present embodiment, the detection channel 21A, which is in this way configured by electrically connecting to each other the pair of radiation detectors 21 adjacent to each other in the Y direction, configures one detection unit (i.e., channel). Consequently, it turns out that, substantially, the channel number in the Y direction will be decreased. Meanwhile, since the number of the detection channels 21A increases in the X direction, the channel number in the X direction can be increased. This, in the PET imaging apparatus 1, makes it possible to increase the channel number in the X direction without increasing the entire channel number. This enhances the spatial resolution of an image acquired. Also, since no increase occurs in the entire channel number, the number of the signal processing circuits will not be increased, either. Accordingly, the heat-liberation increase in the signal processing circuits will be suppressed. This makes it possible to shorten the inspection time. The enhancement in the spatial resolution prevents occurrence of the high power consumption, and further, makes it possible to use the large-scale-produced detector assembly structures 41 just as they are. Consequently, it becomes possible to enhance the spatial resolution with the cost suppressed at the same time.

(2) The detection element 211 includes the cathode C on one surface of the semiconductor element S, and the anode A on the other surface thereof. The detector assembly structure 41 is configured by arranging in parallel the plurality of detection elements 211 in the state where the cathodes C and the anodes A are arranged in the X direction. Accordingly, it becomes possible to divide the detector assembly structure 41 in the X direction in the unit of the detection elements 211 (e.g., the detector 21 including the two detection elements 211). This makes it possible to detect the radiation for each of the divided regions (e.g., the detector 21). Consequently, the detection area can be fragmented in the X direction. This makes it possible to enhance the spatial resolution. Furthermore, between a detector 21 and another detector 21 which is adjacent to the detector 21 in the Y direction on the wiring board 24, either the cathode electrodes C or the anode electrodes A are electrically connected to each other, thereby forming one detection channel 21A. As a result, the pair of adjacent detectors 21 can each be used as the one detection channel 21A which is formed in a long manner in the Y direction. Consequently, the radiation becomes easier to capture in each detection area.

(3) In each detector 21, the cathodes C or the anodes A of the detection elements 211 are arranged such that the cathodes C or the anodes A will be in a mutually-facing state. This makes it possible to co-use the electrically conductive members 22, 23 between the adjacent detectors 21. Accordingly, there is no need of arranging an electrically insulating martial between the mutual detection elements 211. This allows implementation of the densely-packed arrangement of the detection elements 211 in the X direction. This, further, allows an enhancement in the sensitivity, and accomplishment of the shortening in the inspection time as well.

(4) The electrically conductive members 22, 23 include overhanging parts 22a, 23a which are part of the electrically conductive members 22, 23, and which protrude onto the outer side than the semiconductor element S. Since the overhanging parts 22a, 23a can be mounted onto the wiring board 24, the electrically conductive members 22, 23 can be easily mounted onto the wiring board 24.

(5) The overhanging parts 22a, 23a can be mounted onto the connection members CP, AP on the wiring board 24 using the electrically conductive adhesive agents 25. This makes it possible to shorten a time needed for connection operation of the overhanging parts 22a, 23a to the connection members CP, AP. The adhesive agents 25 exhibit both functions of the electrical connection and mechanical connection (holding) between the detectors 21 and the wiring board 24. Also, the terminal parts 22b, 23b, which are perpendicularly suspended from the overhanging parts 22a, 23a, are formed into the narrower width so that the overhanging amounts of the terminal parts 22b, 23b become smaller than those of the overhanging parts 22a, 23a. This makes it possible to suppress the scattering of γ-rays down to the lowest possible degree in the region of the terminal parts 22b, 23b. Also, the heat conducted from the wiring board 24 to the detectors 21 decreases by the amount equivalent to the narrower-width formation of the terminal parts 22b, 23b. This enhances stability of the detectors 21.

(6) The electrically conductive members 22, 23 are composed of an electrically conductive metal, i.e., an electrically conductive material having rigidity. Accordingly, the electrically conductive members 22, 23 also function as protection members for the semiconductor elements S. In particular, when the semiconductor elements S are composed of a mechanically-fragile semiconductor material such as CdTe, CZT, or GaAs, the electrically conductive members 22, 23 make it possible to prevent damage of the semiconductor elements S.

(7) Since the overhanging parts 22a, 23a protrude on the different two sides of the detector 21, it becomes possible to enhance the electrically insulating property of the detection module 20A. Also, the detection channel 21A can be easily configured by connecting the overhanging parts 23a of the adjacent detectors 21 to the connection members AP respectively. The detection channel 21A can be configured on the wiring board 24 by a task which is basically the same as the task at the time when implementing the detectors 21 on the wiring board 24 when the detection channel 21A like this is not configured. Accordingly, it becomes possible to configure the detection channel 21A on the wiring board 24 without performing the special implementation task.

(8) Since the respective detectors 21 are arranged such that the overhanging parts 22a, 23a will be directed into the Y direction, it becomes possible to narrow the spacing between the mutual detectors 21 in the X direction. Accordingly, it becomes possible to reduce the ratio of γ-rays which will merely pass through the spacing without being captured and detected by the detectors 21. This allows an enhancement in the γ-ray detection efficiency, and also allows an enhancement in the spatial resolution of an image acquired.

(9) In the X direction, on both-side regions of the respective detectors 21, the same-polarity electrodes 22 are arranged in a mutually-facing state. This arrangement makes it possible to reduce the insulation between the mutual detectors 21 in the X direction, thereby making it possible to narrow the spacing between the mutual detectors 21 in the X direction. This, similarly to the above-described (8), allows an enhancement in the γ-ray detection efficiency, and also allows an enhancement in the spatial resolution of an image.

(10) In all of the detectors 21 which are adjacent to each other in the Y direction, the overhanging parts 22a or 23a connected to the same-polarity electrodes (i.e., the anodes A or cathodes C) are arranged such that the overhanging parts 22a or 23a will be in a mutually-facing state. This arrangement makes it possible to reduce the insulation between the mutual detectors 21 in the Y direction, thereby making it possible to narrow the spacing between the mutual detectors 21 in the Y direction. This, consequently, allows an enhancement in the γ-ray detection efficiency, and allows an enhancement in the spatial resolution of an image. Here, the arrangement such that the overhanging parts 22a, 23a are in the mutually-facing state includes not only the case where the overhanging parts 22a, 23a of the mutual detectors 21 in the mutually-facing state are in the mutually-facing state completely, but also the case where the mutual detectors 21 in the mutually-facing state are shifted in the X direction perpendicular to the Y direction and thus positions of the overhanging parts 22a, 23a are shifted in the X direction. Concretely, a state where the sides on which the overhanging parts 22a, 23a protrude in the detectors 21 which are adjacent to each other in the Y direction are in the mutually-facing state is the state where the overhanging parts 22a or 23a are arranged such that the overhanging parts 22a or 23a are in the mutually-facing state.

(11) The detectors 21 are set up on both sides of the wiring board 24. As a result, it becomes possible to reduce the number of the wiring boards 24 down to the one-half in the PET imaging apparatus 1. Accordingly, it becomes possible to enhance the arrangement density of the detectors 21 in the PET imaging apparatus 1. This allows implementation of further enhancements in the γ-ray detection efficiency and the spatial resolution of an image.

(12) The detection module 20A and the ASIC board 20B are mounted onto each other in a freely detachable/attachable manner. Consequently, if either of them fails, either the failed detection module 20A or the failed ASIC board 20B can be easily replaced.

(13) In the PET imaging apparatus 1 including the detection channels 21A, the signal processing circuits are formed by using the ASICs that include a large number of built-in amplification circuits (one for each detection channel 21A) which individually correspond to each detection channel 21A. This makes it possible to deal with the downsizing implementation of each detection channel 21A, and eventually, an increase in the number of the detection channels 21A. As a result, it becomes possible to enhance the spatial resolution further.

(14) It is possible to configure the detection module 20A where the detection channels 21A including the high energy-resolution detectors 21 can be arranged in large number. This allows implementation of the high quantitative-property inspection in the 3-D imaging.

(15) It is possible to prevent the dielectric breakdown of the detection channel 21A by coating the detectors 21 set up on the wiring board 24 with an electrically insulating material.

(16) The overhanging parts 22a in the two detection channels 21A which are adjacent to each other in the Y direction are connected to the connection member CP (e.g., connection member CP1). Accordingly, it becomes possible to enhance the arrangement density of the detection channels 21A in the Y direction. This also allows the enhancements in the γ-ray detection efficiency and the spatial resolution of an image. Also, this configuration makes it possible to shorten the length of the wiring board 24 in the Y direction, and thereby to shorten the length of the PET imaging apparatus 1 in the radial direction. This leads to accomplishment of the compact implementation of the PET imaging apparatus 1. The arrangement of the detectors 21 indicated in the above-described (10) also makes it possible to shorten the length of the wiring board 24 in the Y direction. This further shortens the length of the PET imaging apparatus 1 in the radial direction, thereby leading to the compacter implementation of the PET imaging apparatus 1. Also, the overhanging parts 22a, 23a of the detectors 21 are connected to the connection member AP, CP in the state where the overhanging parts 22a, 23a are overlapped with each other. Implementing this configuration makes it possible to further narrow the spacing between the mutual detectors 21 which are adjacent to each other in the Y direction. Accordingly, it becomes possible to further enhance the arrangement density of the detectors 21 in the Y direction on the wiring board 24. This allows implementation of the downsizing in the PET imaging apparatus 1. This, further, makes it possible to decrease areas of the connection member AP, CP on the surface of the wiring board 24, thereby allowing prevention of the dielectric breakdown therebetween.

(17) The wiring 24a, which is connected to the connection member CP and is co-used among the plurality of connection members CP, is provided on the wiring board 24. This makes it possible to lower the wiring density of the wirings 24a, 24b provided on the wiring board 24. Consequently, it becomes easy to perform the wiring task in the wiring board 24.

(18) The surface of the wiring board 24 onto which the detectors 21 are mounted is arranged in a manner of being directed into the longitudinal direction of the bed 31. Accordingly, it becomes possible to arrange the detectors 21 in a densely-packed manner in the circumferential direction (i.e., X direction) of the PET imaging apparatus 1. This makes it possible enhance the γ-ray detection efficiency and the spatial resolution of an image.

(19) As described earlier, it is possible to narrow the spacing between the mutual detectors 21 in the Y direction (i.e., radial direction of the PET imaging apparatus 1). This shortens the distances between the inspection target H and the detectors 21 on the Y-direction back-stage side. This brings about an effect of enhancing the γ-ray detection sensitivity in the PET imaging apparatus 1.

(20) In the present embodiment, the two detection channels 21A are configured using a pair of the detector assembly structures 41 arranged in a manner of being adjacent to each other in the Y direction, then mounting the detector assembly structures 41 onto the wiring board 24. This makes it possible shorten the task time need for mounting the detectors 21 onto the wiring board 24.

In the above-described embodiment, the overhanging parts 23a of the electrically conductive members 23 connected to the anode A are connected to the connection member AP (wiring), and the overhanging parts 22a of the electrically conductive members 22 connected to the cathode C are connected to the connection member CP (wiring). It is also possible, however, to connect the overhanging parts 23a to the connection member CP, and to connect the overhanging parts 22a to the connection member AP. In this case, the cathode C becomes an electrode for outputting the γ-ray detection signal, and the anode A becomes an electrode for applying the bias voltage. As long as the bias voltage applied between the anode A and the cathode C is a reverse-direction voltage, either of these patterns is implementable.

Also, the electric potential at the anode A and the electric potential at the cathode C have been set at substantially the ground potential and −500 V, respectively. No limitation, however, is imposed on the electric potentials as long as the voltage is the reverse-direction voltage. Accordingly, the voltage values may be set within a range which permits the PET imaging apparatus 1 to operate normally. Incidentally, it is also possible to employ the cathode C as the extraction electrode for extracting the radiation detection signal, and the anode A as the application electrode for applying the bias voltage.

Furthermore, the cathodes C are arranged on both end sides of the detector assembly structure 41, respectively. Meanwhile, the above-described four detection elements 211 may also be arranged such that the anodes A are arranged on both end sides of the detector assembly structure 41.

Also, although the detector assembly structure 41 is configured by arranging the four detection elements 211 in parallel, the number of these in-parallel detection elements 211 need not be limited to the four. In order to enhance the electrically insulating property in the X direction, however, it is preferable to configure the one detector assembly structure 41 using the detection elements 211 in an even number.

In the above-described embodiment, as illustrated in FIG. 4 to FIG. 7, the connection members AP and the connection members CP are also provided in regions other than the ones onto which the adhesive agents 25 are connected. These connection members AP and connection members CP, however, may also be formed into a minimum essential area onto which the adhesive agents 25 are able to be connected. Moreover, depending on the requirements, the connection may be established inside the wiring board 24. This allows the electrically insulating property to be enhanced between the connection members AP and connection members CP and the electrodes corresponding thereto on the surface of the wiring board 24.

In the above-described embodiment, the two detection channels 21A are configured using the pair of the detector assembly structures 41 arranged in the manner of being adjacent to each other in the Y direction. It is also allowable, however, to configure the detection channels 21A not by using the detector assembly structures 41 but by using a pair of the detectors 21 arranged in the manner of being adjacent to each other in the Y direction. In this case, the detectors 21 of the detection channels 21A which are adjacent to each other in the X direction need to be arranged with a spacing provided therebetween. As a result, this configuration slightly lowers the densely-packed implementation of the detectors 21 in the X direction as compared with the above-described embodiment using the detector assembly structures 41. This configuration, however, increases the spatial resolution in the X direction as compared with the conventional case.

Incidentally, in the embodiments described so far, the explanation has been given selecting the PET apparatus (refer to FIG. 1A) as an example of the radiological imaging apparatuses. Being not limited to the PET apparatus, however, the detectors and the detection modules according to the present invention are also applicable to the SPECT (: Single Photon Emission Computer Tomography) apparatus and the y camera. In this connection, although imaging of the three-dimensional functional image of an inspected patient is common to the PET apparatus and the SPECT apparatus, the SPECT apparatus cannot perform the simultaneous measurement since its measurement principle is the single-photon detection. On account of this, the SPECT apparatus is equipped with a collimator for regulating the incident position (angle) of γ-rays. Also, the y camera acquires only the functional image which is of two-dimensional mode, and is equipped with a collimator for regulating the incident angle of γ-rays.

Incidentally, it is also allowable to select a configuration of the radiological imaging apparatus where the PET apparatus or the SPECT apparatus and the X-ray CT are combined with each other.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A radiation detection module, comprising:
a plurality of radiation detectors, and
a wiring board on which said plurality of radiation detectors are mounted in a manner of being arranged in a first direction and in a direction which is perpendicular to said first direction, wherein
each of said radiation detectors is configured by arranging a plurality of semiconductor detection elements in parallel in said direction perpendicular to said first direction, each of said semiconductor detection elements having a cathode electrode on one surface thereof and having an anode electrode on the other surface thereof,
said radiation detection, module further comprising:
a plurality of detection channels, each of said detection channels being mounted on said wiring board and including a pair of said radiation detectors which are adjacent to each other in said first direction, each of said detection channels formed by electrically connecting together said cathode electrodes of said pair of said radiation detectors or electrically connecting together said anode electrodes of said pair of said radiation detectors.

2. The radiation detection module according to claim 1, wherein
said cathode electrodes of said pair of said radiation detectors are electrically connected to each other via electrically conductive materials provided on said wiring board, or said anode electrodes of said pair of said radiation detectors are electrically connected to each other via electrically conductive materials provided on said wiring board.

3. The radiation detection module according claim 2, wherein
said pair of said radiation detectors, which are adjacent to each other in said first direction, are mounted onto said wiring board such that respective connection parts of electrodes to be electrically connected to each other are in a mutually-facing state.

4. The radiation detection module according to claim 3, wherein
said connection parts are provided on a mutually-facing surface side of said adjacent radiation detectors in a manner of protruding from said mutually-facing surface side.

5. The radiation detection module according to claim 2, wherein
said electrically conductive materials are wirings or electrically conductive members.

6. The radiation detection module according to claim 1, wherein
said semiconductor detection elements are composed of any one of CdTe, CdZnTe, and GaAs.

7. A radiation detection module, comprising:
a plurality of radiation detectors, and
a wiring board on which said plurality of radiation detectors are mounted in a manner of being arranged in a first direction and in a direction which is perpendicular to said first direction, wherein
each of said radiation detectors is configured by arranging a plurality of semiconductor detection elements in parallel in said direction perpendicular to said first direction, each of said semiconductor detection elements having a cathode electrode on one surface thereof and having an anode electrode on the other surface thereof,
said radiation detection module further comprising:
a plurality of detection channels, each of said detection channels being mounted on said wiring board and including a pair of said radiation detectors which are adjacent to each other in said first direction, each of said detection channels formed by electrically connecting together said cathode electrodes of said pair of said radiation detectors or electrically connecting together said anode electrodes of said pair of said radiation detectors,
connection parts of said cathode and anode electrodes including overhanging parts and terminal parts, said overhanging parts overhanging from a lower portion of said radiation detectors on a mutually-facing surface side thereof into a mutually-facing direction, said terminal parts being perpendicularly suspended from said overhanging parts, said radiation detectors being mounted onto a board surface of said wiring board by said terminal parts without contact between said board surface and said radiation detectors.

8. The radiation detection module according to claim 7, wherein each of said radiation detectors is configured by arranging said plurality of semiconductor detection elements in parallel in said direction perpendicular to said first direction in a state where said electrodes of same polarity face to each other alternately.

9. A printed circuit board, comprising:

a wiring board, a plurality of detection channels, each of said detection channels being provided in a first area of said wiring board and including a plurality of radiation detectors, and signal processing apparatuses, each of said signal processing apparatuses being provided in a second area of said wiring board, and being connected to each of said detection channels individually, wherein said plurality of radiation detectors are arranged in a first direction and in a second direction in plural number, respectively, said first direction heading from said first area to said second area, said second direction being perpendicular to said first direction, each of said detection channels being configured by electrically connecting to each other a pair of said radiation detectors which are adjacent to each other in said first direction a plurality of detector assembly structures are arranged in said first direction and in said second direction in plural number, respectively, each of said detector assembly structures including said plurality of radiation detectors, each of said detector assembly structures being configured by electrically connecting to each other said electrodes of same polarity of said plurality of radiation detectors, said detection channels being configured by electrically connecting to each other said radiation detectors included in each of a pair of said detector assembly structures which are adjacent to each other in said first direction, and accordingly at least two of said detection channels being formed in said pair of said detector assembly structures.

* * * * *